United States Patent [19]

Blakeley et al.

[11] Patent Number: 4,991,587

[45] Date of Patent: Feb. 12, 1991

[54] ADAPTIVE FILTERING OF PHYSIOLOGICAL SIGNALS IN PHYSIOLOGICALLY GATED MAGNETIC RESONANCE IMAGING

[75] Inventors: Douglas M. Blakeley, Euclid; James J. Rogers, University Heights, both of Ohio

[73] Assignee: Picker International, Inc., Highland Heights, Ohio

[21] Appl. No.: 439,855

[22] Filed: Nov. 21, 1989

Related U.S. Application Data

[63] Continuation-in-part of Ser. No. 98,546, Sep. 18, 1987, abandoned, which is a continuation of Ser. No. 764,440, Aug. 9, 1985, Pat. No. 4,694,837.

[51] Int. Cl.[5] .............................................. A61B 5/055
[52] U.S. Cl. ............................. 128/653 A; 128/653 R; 128/670; 128/671; 128/696; 128/901
[58] Field of Search ........ 128/653 R, 653 A, 653 SC, 128/69 S, 696, 670, 671, 700, 708, 901; 324/318, 322

[56] References Cited

U.S. PATENT DOCUMENTS

| | | | |
|---|---|---|---|
| 3,848,586 | 11/1974 | Suzuki et al. | |
| 3,968,430 | 7/1976 | Maas | 128/901 X |
| 4,038,536 | 7/1977 | Feintuch | 128/696 |
| 4,537,200 | 8/1985 | Widrow | 128/696 |
| 4,545,384 | 10/1985 | Kawachi | 128/653 |
| 4,716,368 | 12/1987 | Haacke | 324/309 |
| 4,761,819 | 8/1988 | Denison et al. | 382/54 |
| 4,763,075 | 8/1988 | Weigert | 324/318 |
| 4,887,609 | 12/1989 | Cole, Jr. | 128/696 |

OTHER PUBLICATIONS

Byrne et al., "Adaptive Filter Processing in Microwave Remote Heart Monitors", IEEE Transactions on Biomedical Engineering, vol. BME-33, No. 7, Jul. 1986, pp. 717-722.

"Cardiac Response to Pulsed Magnetic Fields with Regard to Safety in NMR Imaging" by McRobbie et al., Phys. Med. Biol., vol. 30, No. 7, pp. 695-702.

Primary Examiner—Ruth S. Smith
Attorney, Agent, or Firm—Fay, Sharpe, Beall, Fagan, Minnich & McKee

[57] ABSTRACT

A patient (B) is disposed in a region of interest of a magnetic resonance apparatus (A). During an imaging sequence, changing magnetic field gradients and radio frequency pulses are applied to the region of interest. The changing magnetic field gradients induce a corresponding electrical response in the patient. Electrodes (40) of a cardiac monitor (C) sense the electrocardiographic signal of the patient as well as the electrical response to the magnetic field gradient changes and produces an output signal having a cardiac component and a noise component. The bandwidth of the noise component varies in accordance with the changes of the magnetic field gradients. An adaptive filter (80) filters the output signal to remove the changing magnetic field gradient induced noise. The bandwidth of the filter function with which the output signal is filtered is varied or adjusted in accordance with the magnetic field gradient changes. The magnetic field gradient changes are monitored (84), their rate of change determined (88), and the bandwidth of the filter function is adjusted (92) in accordance with the rate of change. Alternately, the magnetic field gradient changes are determined a priori from a knowledge of the imaging sequence. As the imaging sequence progresses, a look-up table (150) is addressed to retrieve preprogrammed filter function information for various views or stages of the imaging sequence.

14 Claims, 4 Drawing Sheets

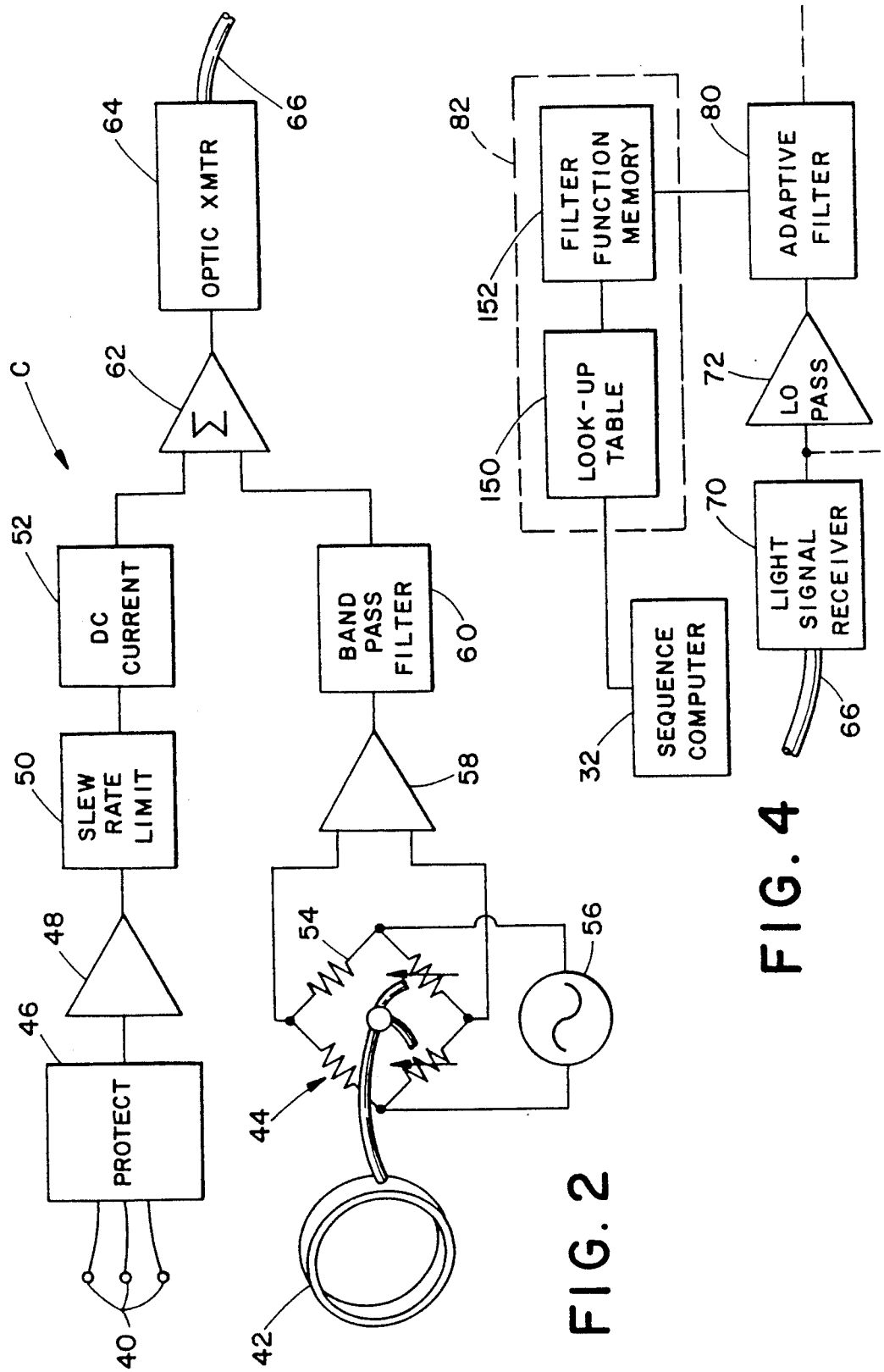

ADAPTIVE FILTERING OF PHYSIOLOGICAL SIGNALS IN PHYSIOLOGICALLY GATED MAGNETIC RESONANCE IMAGING

This application is a continuation-in-part of U.S. application Ser. No. 098,546, filed Sept. 18, 1987, now abandoned which in turn is a continuation of application Ser. No. 764,440, filed Aug. 9, 1985, now U.S. Pat. No. 4,694,837.

BACKGROUND OF THE INVENTION

The present invention relates to the art of non-invasive anatomical examination. It finds particular application in conjunction with cardiac and respiratory gated magnetic resonance imaging and will be described with particular reference thereto. However, it is to be appreciated that the invention may have application in other non-invasive examination techniques in which the examination is controlled, gated, or modified in accordance with anatomical motion.

Magnetic resonance imaging sequences commonly include the application of a radio frequency pulse concurrently with a slice select pulse in order to excite magnetic resonance in a selected slice of the patient or subject. A phase encode gradient pulse is applied to encode phase into the resonating nuclei. Another radio frequency pulse is applied, either before or after the phase encode gradient pulse, to invert the magnetic resonance and cause a magnetic resonance echo. A read gradient pulse is applied during the echo to provide a second dimension of encoding in the retrieved magnetic resonance signal or view. Commonly, this sequence is repeated a multiplicity of times, each time with a different amplitude phase encode gradient in order to generate a corresponding multiplicity of differently phase encoded views.

Anatomical movement, such as cardiac and respiratory motion tend to degrade the resultant images. The amount of degradation is related to the amount or magnitude of physiological displacement from view to view, the rate of movement, and the like. Various anatomical condition monitors have been utilized to control the collection, processing, or use of magnetic resonance and other noninvasive imaging data in accordance with physiological motion. See for example U.S. Pat. Nos. 4,763,075 to Weigert and 4,545,384 to Kawachi.

A patient's cardiac cycle is normally sensed with electrocardiographic electrodes mounted to the patient's skin and connected by electrical leads with processing circuitry. In magnetic resonance imaging, the changing gradient magnetic fields induce an electrical response in the patient as well as in the electrocardiographic leads. This electrical response becomes superimposed on the electrocardiographic signal.

Conventionally, the magnetic resonance field gradients were applied as square pulses. A square pulse is the sum of sine waves—predominantly high frequency sine waves. The frequency content of the noise induced by square gradient pulses was significantly higher than the R-wave portion of the cardiac signal, the highest frequency portion of a normal cardiac signal. This difference in frequency enabled the R-wave and the gradient pulse induced noise to be separated, e.g. with a slew rate filter.

One of the problems with square gradient pulses is that they are relatively energy consumptive. It has been found that utilizing more rounded gradient pulses produces equally good images, but with significantly less energy. However, rounding the square wave pulses has reduced their frequency content. More significantly, the electrical response induced in the patient and leads by the rounded gradient pulses includes significant components that have a frequency in the same range as the frequency of the R-wave.

The present invention contemplates a new and improved anatomical gating system which overcomes the above referenced problems and others.

SUMMARY OF THE INVENTION

In accordance with one aspect of the present invention, a monitored cardiac signal is filtered with a filter function that is selectively adjusted in accordance with magnetic field gradients applied.

In accordance with a more limited aspect of the present invention, the filter is selected in accordance with the view. Views with a large phase encode gradient are filtered more heavily than views with a small phase encode gradient.

In accordance with another more limited aspect of the invention, the filter function is calculated in accordance with the magnitude of gradient applied. The filter function is controlled by monitoring applied gradient fields. Alternately, the filter function may be retrieved with a look-up table in accordance with the number or phase encoding of the most recent view.

In accordance with another limited aspect of the invention, the bandwidth of the filter function is adjusted with the bandwidth of the noise.

One advantage of the present invention is that the imposed filtering is adaptive. That is, the amount of filtering varies as needed for each monitored cardiac cycle.

Another advantage of the present invention is that it facilitates the use of less power consumptive rounded gradient pulses in conjunction with anatomical monitoring and gating.

Another advantage of the present invention is that it eliminates over filtering. Each cardiac pulse is filtered only to the extent necessary.

Still further advantages will become apparent to those of ordinary skill in the art upon reading and understanding the following detailed description of the preferred embodiments.

BRIEF DESCRIPTION OF THE DRAWINGS

The invention may find form in various components and arrangements of components and in various steps and arrangements of steps. The drawings are only for purposes of illustrating a preferred embodiment and are not to be construed as limiting the invention.

FIG. 2 is a diagrammatic illustration of the cardiac and pulmonary monitoring apparatus of FIG. 1;

DETAILED DESCRIPTION OF THE PREFERRED EMBODIMENT

Figure 1:
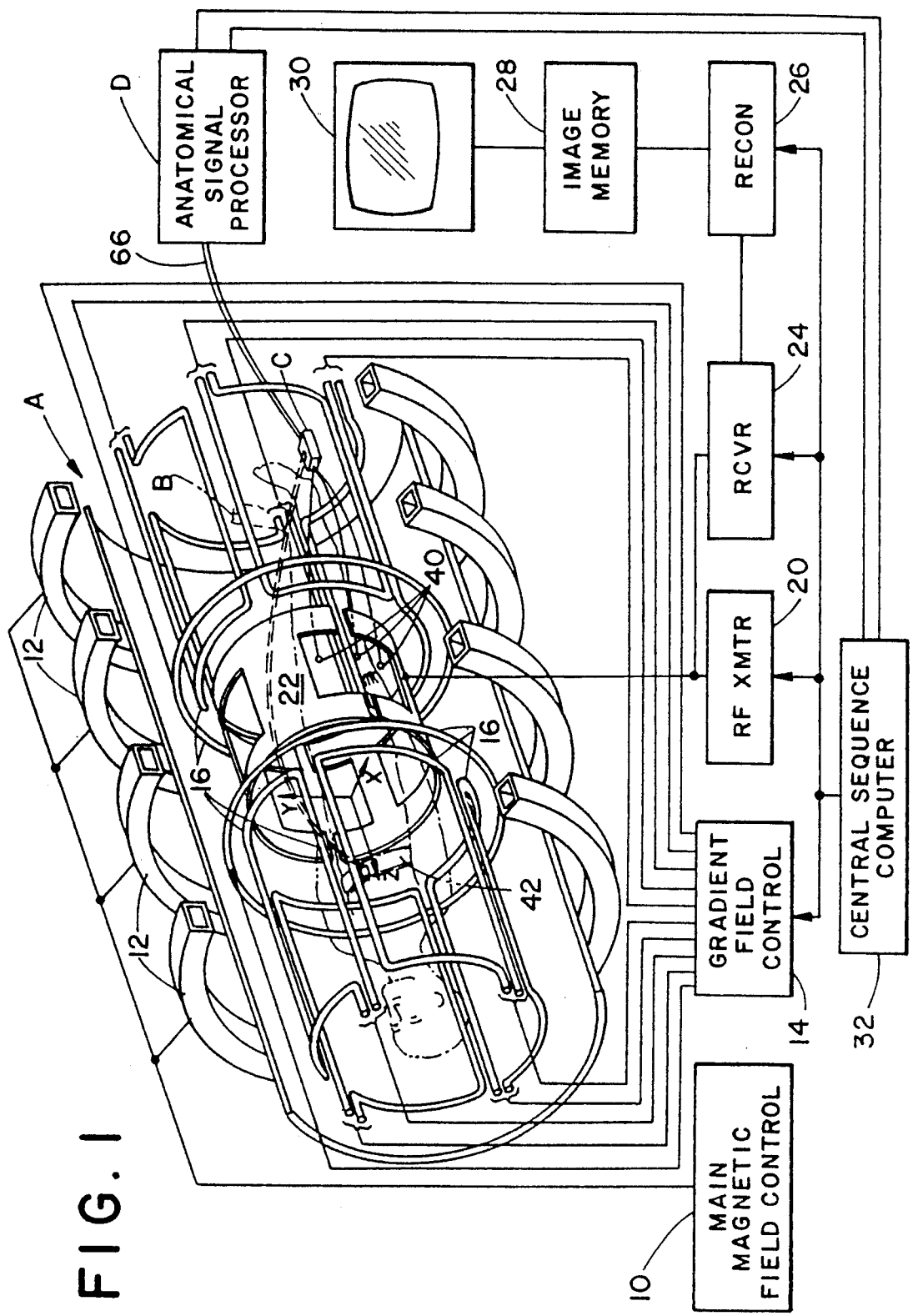
FIG. 1 is a diagrammatic illustration of a magnetic resonance imaging apparatus in accordance with the present invention.

With reference to FIG. 1, a non-invasive examination apparatus A, such as a magnetic resonance imaging apparatus, receives a subject, particularly a patient B who is to undergo a non-invasive examination. An monitoring means 0 is disposed adjacent the subject and interconnected with a remote condition signal processing means D. The monitoring means monitors a preselected condition of the subject, such as cardiac and respiratory cycles or other anatomical conditions. An output signal from the monitor conveys monitored condition information on which a noise component attributable to changing non-invasive examination parameters is superimposed. The processing means D derives monitored condition information, such as anatomical motion and cardiac gating information from the received data. The processing means also filters the output signal with an adaptive filter function that is regularly readjusted during each examination to provide the most appropriate filter function for removing the currently induced noise component. The information is conveyed to the magnetic resonance imaging apparatus A for use in controlling the timing of the imaging sequence, the processing of collected resonance data, the collection or filtering of magnetic resonance data, and the like.

The magnetic resonance imaging apparatus includes a main magnetic field controller 10 which controls resistive or superconducting main magnetic field coils 12 to generate a substantially uniform magnetic field longitudinally through an imaging region. A magnetic field gradient control means 14 applies appropriate current pulses to gradient field coils 16 to create gradients across the main magnetic field. The exact nature and sequence of the gradients is determined by which of the many magnetic imaging sequences is chosen. A radio frequency transmitter 20 generates magnetic resonance excitation, inversion, and manipulation pulses which are applied to a radio frequency coil 22. The gradient and radio frequency pulse sequences are conventional in the art. A radio frequency receiver 24 receives radio frequency magnetic resonance signals from the subject in the examination region. The resonance signals may be picked up by the radio frequency coil 22 or by localized reception coils (not shown). A reconstruction means 26 utilizes a two dimensional inverse Fourier transform or other known algorithm to construct an electronic image representation from the received magnetic resonance signals. Generally, each echo or other signal is reconstructed into one view, which views are summed into an image memory 28. Completed images in the image memory may be displayed on a video display monitor 30, subject to further processing, or archived on tape or disk.

A magnetic resonance sequence control means 32 controls the timing with which the gradient field control means and the radio frequency transmitter apply gradient and radio frequency pulses in order to implement one of the conventional magnetic resonance imaging sequences. The timing or spacing between repetitions of the pulse sequence may be adjusted such that each sequence is taken within a preselected range of anatomical motion. Alternately, the radio frequency receiver 24 or the reconstruction means 26 may be controlled to discard data taken during inappropriate ranges of anatomical movement, subject such data to heavier filtering, replace such data with the average of adjoining views, or the like.

With reference to FIG. 2, the patient monitor means C includes a first condition detector, in the preferred embodiment, ECG electrodes 40 for monitoring the patient's cardiac cycle and generating an electrocardiogram signal indicative thereof. The electrodes, which are attached to the patient in a known manner, pick up not only electrocardiogram signals but also electrical signals induced in a current loop including the patient's body and the electrodes by the changing magnetic field gradients. The output signal of the monitor thus has this gradient induced noise superimposed on the cardiac information. A second anatomical condition detector, in the preferred embodiment a respiratory cycle monitoring means 42, monitors the patient's respiratory cycle. The respiratory monitor is an air-filled elastomeric belt which expands and contracts with the patient's breathing. The expansion and contraction causes corresponding changes in air pressure that are converted into electrical signals indicative of the patient's respiratory cycle by a bridge circuit 44.

A protection circuit 46 filters RF signals sensed by the electrodes, as well as limits the amount of current that would flow through the leads in the event of defibrillation of the patient. An amplifier 48 adjusts the magnitude of the cardiac signals. A slew rate limiting means 50 filters or removes high frequency components that are not normally found in cardiac signals but which are commonly induced as noise in the magnetic resonance imaging environment. A DC correction means $2 removes DC offset.

The balanced bridge pressure to electrical signal transducer 44 includes a bridge circuit $4 across which an oscillator $6 applies a two kilohertz carrier signal. The carrier signal modulates the respiratory signal to bring it into a frequency range that is readily separated from the cardiac signals. A beat pattern or amplitude variation of the modulated signal carries the encoded respiratory cycle data. An amplifier $s amplifies the modulated signal and a band pass filter 60 removes noise and distortion signal components.

A summing means 62 adds or combines the respiratory and cardiac signals with other superimposed noise to produce the output signal. A fiber optic transmitter 64 converts the output signal into an optical signal for generating a light or other non-electric signal. In the preferred embodiment, the frequency of light signals from a light source is modulated in proportion to the magnitude of the voltage of the output signal from the combining means 62 and conveyed along a fiber optic transmission line 66.

Figure 3A:
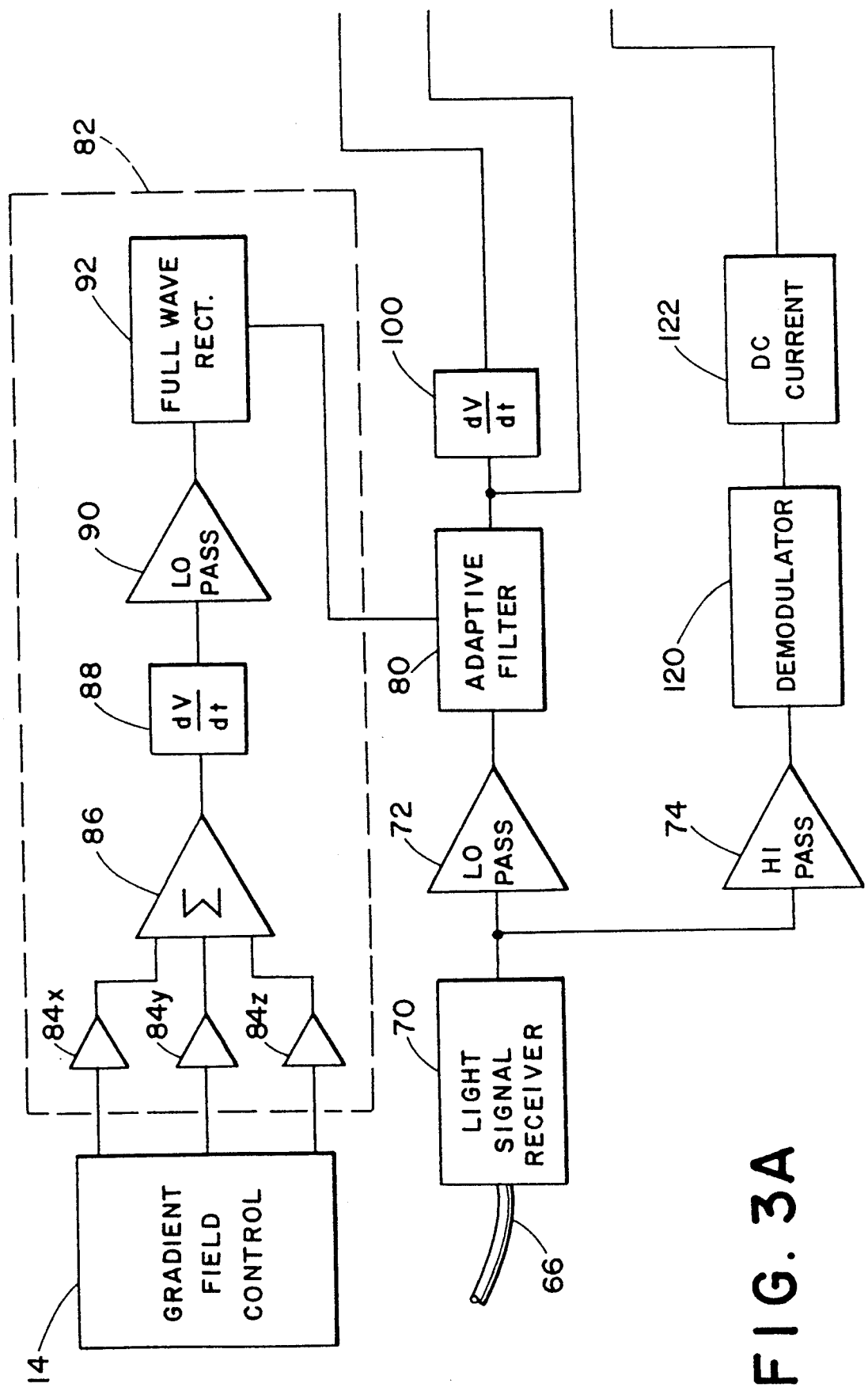
FIG. 3 is a diagrammatic illustration of the cardiac and pulmonary signal processing apparatus of FIG. 1; and, FIG. 4 is an alternate embodiment of the signal processing apparatus of FIG. 3.
Figure 3B:
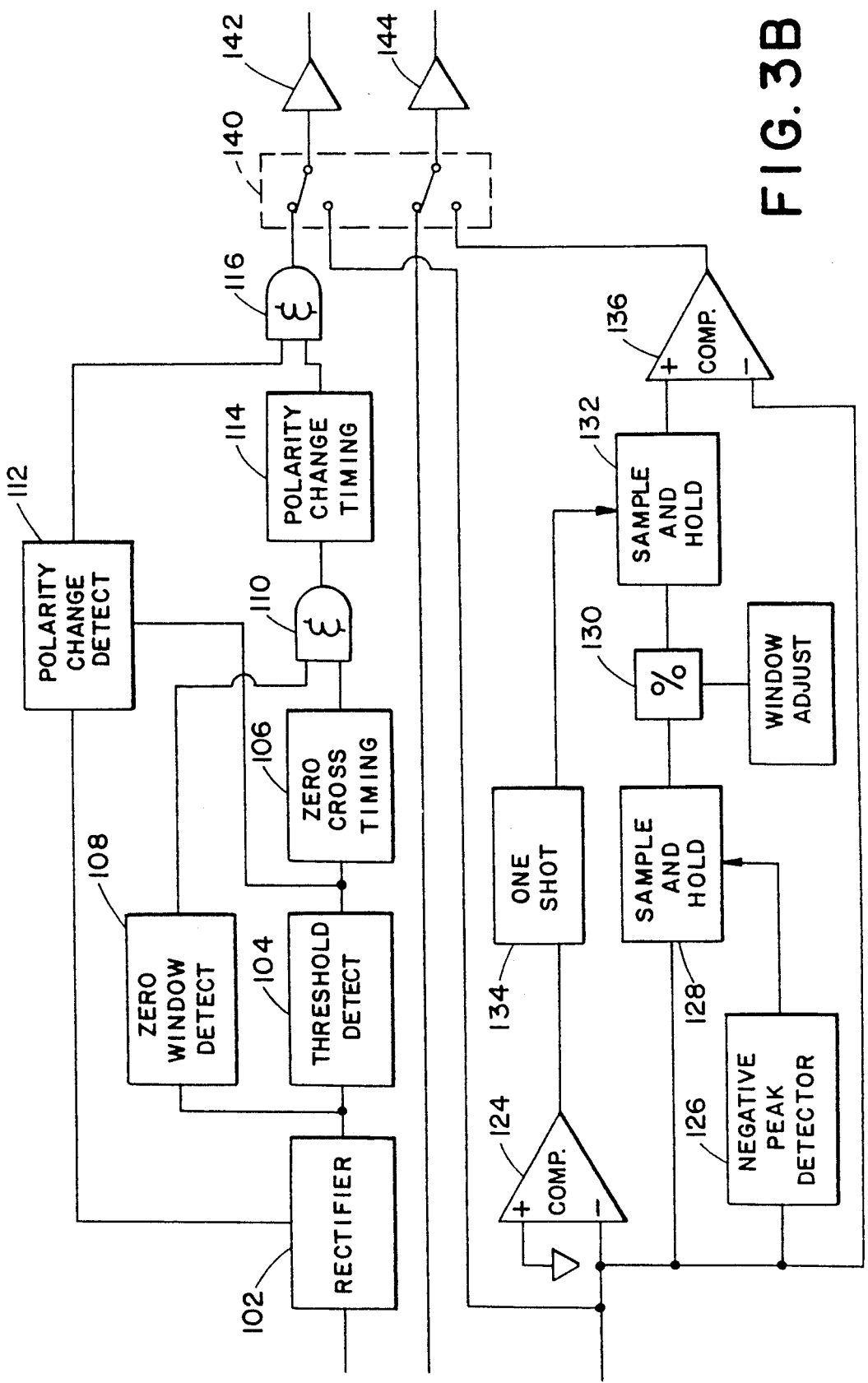

With reference to FIG. 3, a light signal receiver 70 receives the light signal from the optic transmission cable 66 and produces a corresponding electrical combined respiratory and cardiac data with superimposed gradient noise signal. A low pass filter 72 and a high pass filter 74 separate the cardiac and respiratory signal components. Optionally, when other anatomical conditions are monitored or when the anatomical conditions are digitally or differently encoded, other signal component separating means may be employed.

An adaptive filter means so filters the received cardiac signal with an adjustable filter function in accordance with the concurrently occurring view. A filter function changing means 82 adjusts the filter function of the filter means in accordance with the correspondingly changing gradient. The electrical pulses from the gradient field control means 14 to the x, y, and z-gradient coils are monitored and adjusted to an appropriate magnitude by differential amplifiers 84x, 84y, and 84z. A summing means 86 sums the three gradients to provide an output signal indicative of the total gradient applied. The induced patient voltage and the monitored noise component vary in proportion with the rate of change of the gradient field. Hence, the amount of noise superimposed on the corresponding cardiac signal also varies with the rate of change of the gradients. A gradient field rate of change determining means 88, such as a differentiator, determines the rate of change of the total of the gradient fields. A low pass filter 90 removes stray, high frequency components and a full wave rectifier 92 rectifies the rate of change signal to produce a filter selection signal whose voltage is proportional to the rate of change of the gradient magnetic fields. The bandwidth of the noise varies with the rate of gradient change. Hence, the rate of change determining means 88 effectively determines the bandwidth of the noise component. The filter function selected by the filter changing means 82 is selected or varied in accordance with the frequency components of the magnetic field gradient pulses and varies with the nature of the gradient field pulses applied by each individual magnetic resonance scanner. In the preferred embodiment, the signal processing is performed using analog components. Alternately, the signal processing may be performed on a digitized signal using digital signal processing components. Appropriate guidelines and mathematics for calculating an appropriate filter function for each gradient pulse is found in Oppenheim, Alan V. and Shafer, Ronald W., *Digital Signal Processing*, Prentice-Hall, 1975, or numerous other texts on digital signal processing. In general, the bandwidth of the filter function or the amount of filtering around the frequencies of the R-wave is adjusted in proportion to the filter selection signal from the filter selection means 82. When the rate of gradient change is large, the cardiac signal is heavily filtered to remove what is anticipated to be substantial noise. When the gradient change rate is relatively small, the cardiac signal is lightly filtered or not filtered at all because the anticipated noise components are relatively small. The filter selection means 82 varies the bandwidth of the filter function proportionally to the bandwidth of the noise. In this manner, the filter function is adjusted to match the bandwidth of the noise that is superimposed on the cardiac signal.

In the preferred embodiment, detection of the occurrence of an ECG R-wave is based on the derivative of the ECG signal and three detection criteria. A derivative means 100 detects the rate of change of the filtered cardiac signal. A rectifier means 102 provides an output signal that is proportional to the rate of change and an indication of the polarity of the change. The first detection criteria consists of a threshold detector 104 which detects when the magnitude of the rectified signal from rectifier 102 exceeds a predetermined value indicating the imminent occurrence of an R-wave. Once the threshold has been exceeded, a second detection criteria consisting of a timing means 106 is started which is preset for a period of time during which a zero crossing of the derivative should occur. A zero window means 108 searches for the next occurrence of the derivative signal within a prescribed value around zero. An AND means 110 produces an output signal if a zero occurs as detected by the Zero Window means 108 within the time prescribed by the timing means 106.

A polarity change detection means 112 receives the polarity signal from the rectifier means. Once the threshold detector 104 is enabled, the polarity of the derivative of the ECG signal is saved in the polarity change detection means 112. The output of the change detection means 112 changes to a high logic state when the polarity of the derivative of the ECG signal has changed from positive to negative or negative to positive. The output of the AND means 110 starts a third detection criteria consisting of a second timing means 114 which is preset for a period of time during which the derivative of the ECG signal must change polarity. A second AND means 116 produces an output if the polarity of the ECG signal changes polarity within the time period prescribed by the timing means 114 such that only the apex of the R-wave and not other portions of the cardiac cycle provide an output signal.

The respiratory signal from the high pass filter 74 is separated from the carrier signal by a demodulator 120. DC correction circuit 122 establishes a Zero level for subsequent peak detection. A comparator means 124 provides logic high output when the respiratory signal is negative in polarity. A negative peak detection means 126 detects the negative peaks of the inverted respiratory signal and gates a sample and hold circuit 128 in accordance therewith. A multiplying means 130 reduces the sampled peak signal by a preselected percentage, e.g. 70%. A second sample and hold circuit 132 stores the percentage of the peak value when a one shot circuit 134 is triggered by a change in polarity of the respiratory signal from negative to positive as indicated by the comparator means 124. A comparing means 136 compares the present value of the respiratory signal with the threshold value from the second sample and hold 132. When the actual respiratory signal is less than the threshold, an enable or high signal is produced which allows data to be taken, accepted, or processed. When the actual respiratory signal is greater than the threshold level, a low signal is produced to block the collection of data or cause collected data to be discarded. This enable/blocking or respiratory gating signal provides a window within which received data may contribute to the resultant image representation. Optionally, data from outside the window may be filtered or otherwise subject to different processing and still contribute to the resultant image.

A selector switch means 140 selects whether the monitor supplies the cardiac signal and the cardiac gating signal or the respiratory signal and the respiratory gating signal to the scanner A. Buffer amplifiers 142 and 144 amplify the selected signals which are transmitted to the sequence control means 32 or other parts of the scanner.

With reference to FIG. 4, in a given magnetic resonance imaging sequence, the gradients which are being applied with each view are known in advance. Thus, rather than deriving the filter function adjustment on the fly from the sensed gradients, filter functions may be precalculated and retrieved in accordance with the most recently preceding view. That is, the sequence control means 32 may provide a digital signal indicative of the view number to a filter function look-up table 150. The look-up table is preprogrammed in accordance with the magnetic field gradients that are to be applied in each of the numbered views to designate the appropriate corresponding filter function. The corresponding filter function is retrieved from a filter function memory or calculating means 152. The entire filter function may be stored in the memory 152, selected filter functions may be stored, and others interpolated, or the guide lines for calculating the filter function may be stored in the memory 152. For example, the view number may be the most significant bits of the look-up table address and the least significant bits may be from a timing clock that is reset at the beginning of each view. The filter function retrieved from the filter function memory or source 152 is loaded into the filter means so and used to process portions of the cardiac signal that are received until the next filter function is addressed or designated.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A non-invasive diagnostic apparatus comprising:
   a means for non-invasively examining an internal region of a subject and generating diagnostic signals indicative thereof;
   a monitoring means for monitoring a condition of the subject generating output signals indicative thereof, the non-invasive examination means causing a noise signal component that changes with changing examination parameters during the non-invasive examination, the noise component being superimposed on the output signal such that the output signal includes both noise and monitored condition information;
   means for detecting the changing examination parameters
   an adaptive filter means for filtering the output signal with a filter that is adjusted in accordance with the detected changing examination parameters.

2. The apparatus as set forth in claim 1 wherein the noise component has a bandwidth that changes with the changing examination parameters and further including a filter changing means for changing a bandwidth of the filter in accordance with the noise component bandwidth.

3. A non-invasive diagnostic apparatus comprising:
   means for subjecting a region of interest of a patient to changing magnetic fields and radio frequency signals in order to induce magnetic resonance of selected nuclei in the region of interest;
   a cardiac monitoring means operatively connected with the patient for monitoring electrocardiographic signals, the changing magnetic fields inducing noise signals which are superimposed on the electrocardiographic signals, such that an output signal of the cardiac monitoring means includes both noise and cardiac cycle information;
   means for detecting the changing magnetic fields;
   an adaptive filter means for filtering the output signal with a filter function that is adjusted in accordance with the detected changing magnetic fields, such that the filter function is adaptively changed with variations in the changing magnetic fields;
   a receiving means for receiving magnetic resonance signals from the region of interest;
   a sequence control means for controlling the application of magnetic field gradients and radio frequency pulses and processing received magnetic resonance signals into diagnostic information, the control means being operatively connected with the filter means to control at least one of diagnostic information processing and magnetic field gradient and radio frequency pulse application in accordance with the adaptively filtered cardiac information received from the adaptive filter means.

4. The apparatus as set forth in claim 3 wherein the means for detecting the magnetic fields includes:
   means for monitoring magnetic field gradients applied to the region of interest; and further including
   means for determining a noise bandwidth corresponding to the changing gradients; and
   means for adjusting the filter function in accordance with the corresponding noise bandwidth.

5. The apparatus as set forth in claim 3 wherein the sequence control means causes the means for subjecting a region of interest of a patient to changing magnetic fields to apply a preselected sequence of gradient pulses across image region and wherein the adaptive filter means includes a lookup table means which is addressed by the selected gradient pulses of each sequence to designate a corresponding filter function and a filter function source for supplying the filter function designated by the look-up table to the filter means for filtering the output signal.

6. The apparatus as set forth in claim 3 wherein the cardiac signal monitoring means is disposed within the changing magnetic fields closely adjacent the region of interest, the cardiac monitor means including an optic transmitter for converting the output signal to an optical signal which is transmitted to an optical receiving means disposed remote from the imaging region, the optical receiving means converting the optical signal back to an electrical signal, the optical receiving means being operatively connected with the adaptive filter means.

7. The apparatus as set forth in claim 6 further including:
   a second anatomical condition monitoring means which generates an second anatomical condition signal;
   a combining means for combining the cardiac cycle information with superimposed noise and the second anatomical condition signal, the combining means being operatively connected with the optic transmitter means such that the second anatomical condition information, cardiac cyclic information, and noise are combined to produce the optical signal;
   a separating means operatively connected with the optical receiving means for separating a cardiac and noise component and a second anatomical condition component from the receiving means electrical signal.

8. A magnetic resonance imaging system for generating a magnetic resonance image representation of a selected region of interest of a subject, the system comprising:
   a magnetic resonance apparatus including:
      a main magnetic field means for creating a substantially uniform main magnetic field through the region of interest;
      a gradient field means for causing magnetic field gradients across the region of interest;
      a radio frequency transmitter for transmitting radio frequency signals into the region of interest for exciting magnetic resonance;

a receiving means for receiving magnetic resonance signals emanating from the region of interest;

a reconstruction means for reconstructing an image representation from the received magnetic resonance signals;

an anatomical condition monitoring means for monitoring an anatomical condition and producing an output signal that includes a monitored anatomical condition signal component and a noise component which noise component is attributable to the magnetic field gradients caused across the image region;

a filtering means for filtering the output signal with a selectable filter function for filtering the noise signal component from the anatomical condition signal component;

a gradient monitoring means operatively connected with a gradient field means for providing a gradient signal that varies in accordance with changes in the magnetic field gradients across the region of interest, the changes in the magnetic field gradients being indicative of a bandwidth of the noise component;

a filter function changing means in accordance with the gradient signal.

9. The system as set forth in claim 8 wherein the filter function of the filtering means includes a band pass filter function that is adjusted in accordance with the bandwidth of the noise component.

10. The system as set forth in claim 9 wherein the gradient signal addresses a preprogrammed look-up table to select a filter function corresponding to the applied magnetic field gradients, and a filter function source means for supplying the selected filter function to the filter means.

11. A method of non-invasive medical investigation comprising:

subjecting a region of interest of a subject to a main magnetic field, magnetic field gradients across the region of interest, and radio frequency signals to excite selected dipoles within the region of interest to resonance;

monitoring an anatomical condition of the patient and producing an output signal which includes an anatomical condition component and a noise component whose bandwidth varies in accordance with the applied magnetic field gradients;

detecting changes in the applied field gradients;

filtering the output signal with a filter function whose bandwidth varies in accordance with the detected changes to filter the noise component and pass the anatomical condition component;

monitoring magnetic resonance signals emanating from the resonating dipoles in the region of interest.

12. The method as set forth in claim 11 further including reconstructing an image representation from the magnetic resonance signals received from excited dipoles in the region of interest.

13. The method as set forth in claim 12 further including controlling at least one of the application of magnetic field gradients and RF signals and processing of magnetic resonance signals in accordance with the anatomical condition component.

14. The method as set forth in claim 13 wherein the anatomical condition monitoring step includes electrically sensing electrocardiographic signals from the subject and noise signals induced in the subject by changing the magnetic field gradients.

* * * * *